United States Patent
Wofford et al.

(10) Patent No.: US 7,228,180 B1
(45) Date of Patent: Jun. 5, 2007

(54) METHODS FOR TREATING VICTIMS OF CEREBROVASCULAR DISEASE

(75) Inventors: Scott Wofford, Abilene, TX (US); Dale L. Phillips, Jr., Abilene, TX (US); Paul Harris, Abilene, TX (US)

(73) Assignee: Stroke Play Ltd., Abilene, TX (US)

( * ) Notice: Subject to any disclaimer, the term of this patent is extended or adjusted under 35 U.S.C. 154(b) by 424 days.

(21) Appl. No.: 10/682,292

(22) Filed: Oct. 9, 2003

(51) Int. Cl.
*A61N 1/18* (2006.01)

(52) U.S. Cl. .......................................... 607/48; 607/46

(58) Field of Classification Search ................ 607/48, 607/46, 68, 72, 74
See application file for complete search history.

(56) References Cited

U.S. PATENT DOCUMENTS

| | | | |
|---|---|---|---|
| 4,019,518 A | | 4/1977 | Maurer et al. |
| 4,323,073 A | | 4/1982 | Ferris |
| 4,324,253 A | | 4/1982 | Greene et al. |
| 4,532,938 A | | 8/1985 | Carlisle |
| 4,926,865 A | | 5/1990 | Oman |
| 5,058,605 A | * | 10/1991 | Slovak ........................ 607/72 |
| 5,300,096 A | | 4/1994 | Hall et al. |
| 5,425,752 A | * | 6/1995 | Vu'Nguyen .................. 607/72 |
| 5,431,625 A | * | 7/1995 | Fabian et al. ................. 604/20 |
| 6,026,328 A | | 2/2000 | Peckham et al. |
| 6,035,236 A | * | 3/2000 | Jarding et al. ................ 607/53 |
| 6,275,735 B1 | | 8/2001 | Jarding et al. |
| 6,493,592 B1 | | 12/2002 | Leonard et al. |
| 6,500,857 B1 | | 12/2002 | Perricone |
| 6,516,226 B1 | | 2/2003 | Bishay et al. |
| 6,522,927 B1 | | 2/2003 | Bishay et al. |
| 6,539,264 B1 | | 3/2003 | Bishay et al. |
| 6,542,780 B1 | | 4/2003 | Leonard |
| 6,549,797 B1 | | 4/2003 | Leonard et al. |
| 6,556,869 B1 | | 4/2003 | Leonard et al. |
| 2004/0073269 A1 | * | 4/2004 | Carroll et al. ................ 607/46 |

OTHER PUBLICATIONS

Chae et al., "Percutaneous, Intramuscular Neuromuscular Electrical Stimulation for the Treatment of Shoulder Subluxation and Pain in Chronic Hempilegia," Case Report , pp. 296-301, Am. J. Phys. Med. Rehabil, (Copyright 2002) vol. 80, No. 4.

(Continued)

*Primary Examiner*—George R. Evanisko
*Assistant Examiner*—Alyssa M. Alter
(74) *Attorney, Agent, or Firm*—McAfee & Taft

(57) ABSTRACT

The current invention provides novel methods for treating victims of cerebrovascular diseases such as stroke. The methods of the current invention rehabilitate weakened and atrophied muscles by applying electrical stimulation to the muscles. Preferably, the electric current cycles between on and off thereby at 10 second intervals thereby stimulating the muscle for 10 seconds and allowing the muscle to relax for 10 seconds. Treatment periods are preferably 15 minutes per day, five days per week. In general, treatments are performed over a 3 to 12 month period. Patients treated according to the disclosed methodology experience significant improvements in their overall quality of life.

63 Claims, 1 Drawing Sheet

OTHER PUBLICATIONS

Dent et al. "Functional electrical stimulation for limb motor dysfunction following stroke," *The Wessex Institute*, 11 pp., Steer 2001; vol. 1: No. 16.

Kaye, "Transcutaneous Electrical Nerve Stimulation," *eMedicine Journal*, 4 pp., Jan. 29, 2002, vol. 3, No. 1.

Renzenbrink et al., "Percutaneous Neuromuscular Electrical Stimulation (P-NMES) for the Treatment of Painful Shoulder Subluxation I Chronic Hemiplegia," Roessingh and Research and Development, *Rehabiliation centre Het Roessignh, Enschede, the Netherlands*. 1 p., No date available but admitted to be prior art.

Publication entitled "Human Motor Nerve Conduction," AD Instruments, 5 pp., Copyright Aug. 2002, Document No. INB09a.

Internet Web page article entitled "Percutaneous electrical nerve stimulation: an alternative to TENS in the management of sciatica.," Ghoname et al., Pain. 2 pp., Nov. 1999; 83(2): 193-9 (www.ncbi.nlm.nih.gov).

Internet Web page article entitled "Electrodes for Functional Electrical Stimulation," *NIH GUIDE*, 3 pp., vol. 25, No. 3, Feb. 9, 1996 (www.grants1.nih.gov).

Internet Web page article entitled "A Discussion of the Madison Protocols for Medium Frequency Stimulation," Ventura, Jr, *Dynamic Chiropractic*, 5 pp. (Jul. 7, 2003), (www.chiroweb.com).

Internet Web page article entitled "Summary of the Different Types of Electrical Stimulation," *Electrical Stimulation E-stim*, 14 pp., No date available but admitted to be prior art (www.injurednewborn.com).

Internet Web page article entitled "Percutaneous Electrical Nerve Stimulation (PENS): A Promising Alternative-Medicine Approach to Pain Management," White et al., 7 pp., *APS Bulletin*, Mar./Apr. 1999, vol. 9, No. 2 (www.ampainsoc.org).

Internet Web page article entitled "Application of Faradic Stimulation," Amanda Lamb and David Ewins, 3 pp. (Oct. 1995), (www.surrey.ac.uk).

Internet Web page publication entitled "Science News Update," *JAMA and the Archives Journals*, 6 pp., Week of Mar. 3, 1999 (www.ama-assn.org).

\* cited by examiner

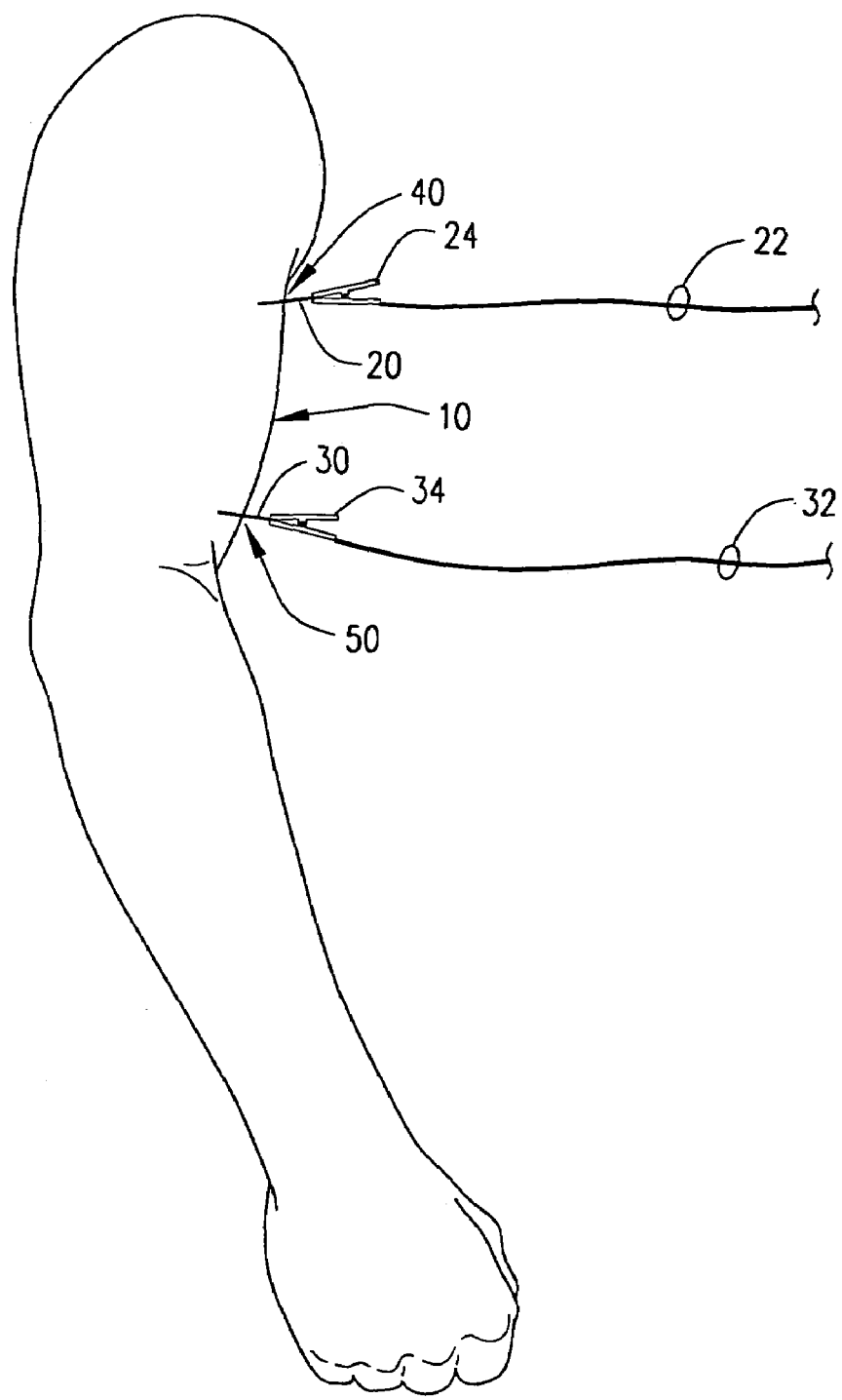
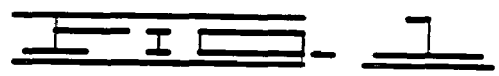

METHODS FOR TREATING VICTIMS OF CEREBROVASCULAR DISEASE

BACKGROUND OF THE INVENTION

Ischemic Cerebrovascular Disease, commonly referred to as stroke, brain attack or cerebrovascular accident, can have a devastating impact on the victim and the victim's family. American Heart Association statistics indicate that there are approximately 500,000 cases of stroke each year and strokes are the leading cause of serious, long-term disability. The likelihood of experiencing a stroke increases with age with approximately 80% of all strokes are suffered by those over the age of 65. Thus, as the average age of American society increases, the number of people at risk for stroke will continue to increase.

In layman's terms, a stroke occurs when a cerebral artery in the brain becomes blocked or ruptures preventing the transport of oxygen and nutrients to the associated portion of the brain. If the brain cells are deprived of oxygen for more than a few minutes they die. With the death of the brain cells, the body function controlled by that portion of the brain is typically lost or at least seriously impaired.

One common method of assessing the impact of stroke on the victim is the Modified Rankin Scale. The Modified Rankin Scale has seven levels of impact ranging from a 0=no symptoms to 6=death. In between the two extremes, lie the following classifications:
- 1=no significant disability despite symptoms: able to carry out all usual duties and activities
- 2=slight disability: unable to carry out all previous activities, but able to look after own affairs without assistance
- 3=moderate disability: requiring some help, but able to walk without assistance
- 4=moderate to severe disability: unable to walk without assistance, and unable to attend to own bodily needs without assistance
- 5=severe disability: bedridden, incontinent, and requiring constant nursing care and attention.

The methods of the current invention are primarily directed to improving the overall function and quality of life in stroke victims with Rankin scores of 2 (slight disability) to 4 (moderate to severe disability).

Several factors impact the patient's recovery from a stroke. In addition to the location and extent of the stroke, the patient's age and overall state of health impact the degree of recovery. The Merck Manual in Chapter 152, Section 14 notes that complete recovery from stroke is uncommon with those patients experiencing early improvements during treatment having a generally better overall prognosis. Typically, 50% of the patients with moderate to severe hemiplegia or milder deficits will recover functionally prior to discharge from the hospital. These individuals may eventually recover sufficiently to care for their own basic needs. Unfortunately, the Merck Manual states, "any deficit remaining after 6 mo is likely to be permanent, although some patients continue to improve slowly."

Research directed toward stroke prevention and treatment of stroke is ongoing; however, progress is slow. In particular, virtually no research is focused on improving the quality of life for stroke victims after the initial rehabilitation process. Rather, a stroke victim with moderate to severe disability more than six months after the occurrence of the stroke is generally regarded as being permanently disability. Clearly, the lack of research directed to improving the quality of life for stroke survivors subsequent to the initial rehabilitation process is a result of the generally accepted view that improvement will not occur in such patients.

The generally accepted view notwithstanding, the current invention provides methods for rehabilitating stroke victims who are well beyond the generally accepted six-month treatment period. The rehabilitation methods of the current invention provide significant improvement in mobility, strength and range of motion to those body parts impacted by cerebrovascular disease. Accordingly, the current invention provides improved methods for treating victims of stroke and in particular for treating victims who continue to suffer disability more than six months following the occurrence of the stroke. The methods of the current invention are described in detail below.

SUMMARY OF THE INVENTION

In one preferred embodiment, the current invention provides a method for restoring functionality to muscles weakened and atrophied by cerebrovascular disease. The method comprises the steps of selecting the muscle to be treated and inserting at least one electrically conductive needle into the area of the proximal motor point and inserting at least one electrically conductive needle into the area of the distal motor point of the muscle. The needles are connected to a source of electricity and the muscle is stimulated by applying an electric current having a carrier frequency of about 2000 Hz to about 4000 Hz to the muscle through the needles.

In another preferred embodiment, the current invention provides a method for restoring functionality to muscles weakened and atrophied by cerebrovascular disease. The method comprises the steps of selecting the muscle to be treated and inserting at least one electrically conductive needle into the area of the proximal motor point and inserting at least one electrically conductive needle into the area of the distal motor point of the muscle. The needles are connected to a source of electricity and the muscle is stimulated by applying an electric current through the needles. The electric current has a carrier frequency of about 2000 Hz to about 4000 Hz and is applied at about 40 to about 60 pulses per second. The pulses have about a 200 to about a 350 microsecond pulse width. The method cycles the application of current between stimulation and rest for a period of up to about 15 minutes, wherein the stimulation period is about 5 seconds to about 50 seconds and the rest period is about 5 seconds to about 50 seconds.

In another preferred embodiment, the current invention provides a method for restoring functionality to muscles weakened and atrophied by cerebrovascular disease. The method comprises the steps of selecting the muscle to be treated and inserting at least one electrically conductive needle into the area of the proximal motor point and inserting at least one electrically conductive needle into the area of the distal motor point of the muscle. The needles are connected to a source of electricity and the muscle is stimulated by applying an electric current through the needles. The electric current has a carrier frequency of about 2000 Hz to about 4000 Hz and is applied at about 40 to about 60 pulses per second. The pulses have about a 200 to about a 350 microsecond pulse width. The method cycles the application of current between stimulation and rest for a period of up to about 15 minutes, wherein the stimulation period is about 5 seconds to about 50 seconds and the rest period is about 5 seconds to about 50 seconds. Typically, the stimulation period includes a 2 second current ramp up and a 2 second current ramp down.

Finally, another preferred embodiment of the current invention provides a method for restoring functionality to muscles weakened and atrophied by cerebrovascular disease. The method comprises the steps of selecting the muscle to be treated and inserting at least one electrically conductive needle into the area of the proximal motor point and inserting at least one electrically conductive needle into the area of the distal motor point of the muscle. The needles are connected to a source of electricity and the muscle is stimulated by applying an electric current through the needles. The electric current has a frequency of about 2500 Hz and is applied at about 50 pulses per second with the pulses having about a 300 microsecond pulse width. The method cycles the application of current between stimulation and rest for a period of about 15 minutes, wherein the stimulation period is about 10 seconds and the rest period is about 10 seconds. Typically, the stimulation period includes a 2 second current ramp up and a 2 second current ramp down. Further the process of cycling the application of current between stimulation and rest is normally repeated at least 3 times per week for a period of about 3 months or longer.

BRIEF DESCRIPTION OF THE DRAWING

The drawing depicts the placement of electrically conducting needles within a bicep in accordance with the practice of the method of the current invention.

DESCRIPTION OF THE PREFERRED EMBODIMENTS

As noted above, physical disabilities produced by a stroke result from the death of brain cells due to oxygen and nutrient deprivation. Accordingly, the location of the stroke will determine the part of the body or function impacted. For example, a stroke in the left hemisphere of the brain will commonly impact the right side of the body. A left hemisphere stroke might produce weakness and/or numbness of the right arm, face or leg. It might also cause a disorder of language (aphasia) as well as visual field deficit (loss of some peripheral vision). In contrast, a right hemispheric stroke typically impacts the left side of the body. This right hemisphere stroke could cause similar problems on the left side although it would be less likely to cause aphasia since few people are truly right hemisphere dominant (99% of right handed people and approximately 85% of left handed people are left hemisphere dominant). In the case of a brainstem stroke virtually any motor deficit is possible. This can vary from one sided weakness to more severe cases in which victims are "locked-in" and can not move any of their extremities. Brainstem strokes can also lead to additional balance and coordination problems. All of these types of strokes produce a potential variety of problems ranging from manual skills involving the upper extremity to gait trouble caused by weakness in the lower extremity. These patients often experience difficulty with normal daily activities like dressing, eating and issues of personal hygiene because of their upper extremity disability. They also frequently suffer from gait, balance and ambulatory difficulties due to their lower extremity weakness. These disabilities also lead to other problems such as painful shoulder subluxations, chronic low back pain and other orthopedic problems arising out of altered skeletal mechanics due to their muscular weakness. The methods of the current invention provide significant long-term improvement in those portions of the body adversely impacted by all types of stroke.

The method of the current invention entails an initial evaluation of the patient by a practitioner qualified in assessing post stroke neurologic deficits. Following the assessment, a treatment plan designed specifically for the muscle groups requiring rehabilitation is formulated. The treatment plan includes the identification of each specific muscle requiring treatment and the type of physical therapy to be used in conjunction with the methods of the current invention.

The present invention stimulates the muscles adversely affected by the stroke by application of an electric current. The electric current enters the muscles through needles penetrating the skin. Preferably, the needles enter the proximal and distal motor points of the targeted muscle. The depth of needle insertion will vary from patient to patient depending on muscle size and any intervening layers of fat. The needle is preferably inserted through any intervening layers of fat and into the "belly" of the muscle at each motor point. While placing the needles near the motor points will suffice, the best results will be obtained when the needles are within or at least as close as possible to the motor points. To ease patient discomfort the preferred embodiment utilizes a single needle for each motor point. In the practice of the current invention, sufficient electric current is used to yield a visible contraction of the muscle. Preferably, the amperage will be set at the patient's maximum pain tolerance level. While lower amperage may produce results, setting the current to the maximum pain tolerance level enhances the overall outcome of the rehabilitation process.

The preferred apparatus for producing the preferred electric current having a carrier frequency of about 2500 Hz is a commercially available device known as a "Russian Stimulation Device." This device was originally developed to increase muscle mass in Russian Olympic athletes. Such devices are readily available from electromethod.com and doctorstore.com. A typical Russian Stimulation Device has two to four channels with each channel having two electrical leads. Thus, many Russian Stimulation Devices are capable of treating four muscles simultaneously.

In the practice of the current invention, the Russian Stimulation Device (referred to herein as an RSD) produces an electric current having a carrier frequency of about 2500 Hz. The current has a biphasic waveform and is delivered at 50 pulses per second with a pulse width of 200 to 300 microseconds. The RSD is preferably provided with the means to cycle the electric current between on and off. Additionally, the RSD preferably has a built in timer directing the device to shut-off after a predetermined period of time.

The following description of the current invention will be described with reference to the drawing. The drawing depicts the bicep muscle 10 with electrically conductive needles 20 and 30 located within the proximal 40 and distal 50 motor points of muscle 10. Although described with regards to a bicep, the method of the current invention can be used in any muscle which has been weakened by cerebrovascular disease. As used herein, a weakened muscle is a muscle no longer receiving normal neural commands from the brain. Additionally, as used herein, the term ischemic cerebrovascular disease refers to strokes, brain attacks, cerebrovascular accidents and cerebral hemorrhages. The methods disclosed herein may also be used to treat the results of other types of brain injury such as those arising from head trauma, infection or anoxia from some cause other than occlusion or rupture of a specific cerebral vessel.

Following determination of the muscles to be treated, the method of the current invention locates the distal 50 and proximal 40 motor points of the muscle. The muscle's motor points are responsible for generating and controlling the contractions of the muscle. When properly stimulated by an electric current, any muscle will experience a contraction as if directed by the brain. To determine the motor points in the muscle to be treated, the skin over the muscle is initially coated with an electro-conductive gel. Such gels are commercially available and generally known to those skilled in the art. A probe connected to the RSD (not shown) is slowly moved over the surface of the skin in the general area of the proximal 40 motor point and over the area of the distal 50 motor point. The current passing through the probe is sufficient to elicit a contraction when the probe passes directly over each motor point. Upon noting the contraction, the operator marks the location of the motor point, preferably with an indelible marker. Following determination of both motor points in the targeted muscle, the gel is removed and the motor points cleaned. In general, swabbing of the motor points with alcohol swabs will be sufficient.

Electrically conductive needles 20 and 30 are preferably inserted into proximal 40 and distal 50 motor points respectively. Any medically appropriate needles having lengths of about 25 mm to about 75 mm are appropriate for use in the practice of the current invention. For example, standard acupuncture needles are suitable for the practice of the current invention.

Following insertion, needles 20 and 30 are connected to the RSD by separate leads 22 and 32. Any means for securely attaching leads 22 and 32 to needles 20 and 30 will suffice. In the initial tests described below, alligator clips 24 and 34 were used to attach leads 22 and 32 to needles 20 and 30. The use of alligator clips 24 and 34 generally do not create any discomfort in the patient and are readily maintained in contact with the needle by taping them to the skin.

A standard RSD delivers an electric current having amperage ranging up to about 25 mA at a carrier frequency of about 2500 Hz. As noted above, the RSD generates an electric current as a biphasic waveform delivered at about 50 pulses per second with a pulse width of 200-350 microseconds. In view of the results obtained by the test cases discussed below, these parameters are the preferred settings for conducting the stimulation treatment. However, an electric current having an amperage ranging from about 1 mA to about 25 mA at a carrier frequency between about 2000 Hz to about 4000 Hz and delivered in the range of about 40 to about 60 pulses per second with a pulse width in the range of about 200 to about 350 microseconds is considered suitable for performing the method of the current invention.

In the preferred method, the RSD cycles between on and off at ten second intervals. Thus, the preferred method repeatedly stimulates the targeted muscle for a ten second period and allows the muscle to rest for a ten second period. While other periods of stimulation and rest may produce adequate results, the ten seconds of stimulation followed by ten seconds of rest produced excellent results that are well tolerated by the patient. During muscle stimulation, the RSD initiates current flow by ramping up the current from an initial 0 mA to a maximum of not more than 25 mA over a two second interval. In the preferred embodiment, the maximum amperage is held for about six seconds and then ramped down to a final of 0 mA over a two second interval prior to halting the current. Alternatively, the electric stimulation step may extend for periods of about 5 to about 50 seconds and the rest periods may extend for periods of about 5 to about 50 seconds. Preferably, the cycle of stimulation and rest continues for a period of up to about 15 minutes on a daily basis for five consecutive days. Typically, the muscle stimulation treatments will be carried out in this manner for about at least a three-month period and may continue for twelve months or longer depending on the progress of the patient. While this is the preferred treatment process, the following description of Patient E's case study results demonstrates that benefits can be produced even when fewer than five treatments per week are administered. Further, administration of the stimulation treatment more than five times per week may be provided; however, patient benefit may be overshadowed by patient discomfort.

The foregoing rehabilitation treatment is repeated for each of the muscles identified in the initial evaluation. Preferably, the treatment is administered by a licensed physical therapist under the supervision of a physician. A licensed physical therapy aide may also be utilized under the direction of the physical therapist. Following completion of the stimulation treatments, needles 20 and 30 are removed and the patient is examined by a physical therapist. The physical therapist evaluates the patient and administers rehabilitative therapy suitable to complement and enhance the benefits of the electro-muscle stimulation. Finally, the patient remains under the care of a physician during the rehabilitation process and is evaluated on typically a monthly basis by the physician.

A further understanding of the benefits of the current invention is provided by the following case summaries reporting the outcome of tests of the current invention on stroke survivors.

Case Studies

Patient A

Patient A, a white male, suffered a left hemispheric stroke in 1994 at the age of 67. The stroke left him with severe right sided weakness. He underwent conventional stroke and rehabilitation care. At the conclusion of his conventional care Patient A required the use of a wheelchair for mobility and had very little use of his right arm. He could, with the help of a leg brace and walker, support his weight sufficiently to allow him to transfer but he could not ambulate. He also required assistance with feeding and personal hygiene. At that time he had virtually no use of his right arm.

In 1996, approximately 18 months after his stroke, Patient A began treatment under the above described methodology. Specifically, the treatment method included the steps of:

determining the muscles to be treated;

coating the skin with electro-conductive gel;

passing, a probe connected to the RSD over the muscle using sufficient current to elicit a muscle contraction thereby indicating the location of a motor point;

marking the motor point;

removing the gel with alcohol swabs;

inserting conductive needles into the proximal 40 and distal 50 motor points;

connecting the needles to the RSD;

applying current having a carrier frequency of 2500 Hz to the needles to stimulate the muscle.

The patient was treated 15 minutes per day, five days a week for approximately twelve months. The muscles treated included quadriceps, hamstrings, biceps, triceps, wrist extensors and wrist flexors. The stimulation step utilized needles for the first three months according to the current method. During the stimulation step, he initially tolerated less than 1 mA, but worked up to approximately 12 mA by the end of the third month. After the third month his stimulation was accomplished using surface pads. He continued to achieve good muscles contractions with the pads and continued to improve. At the conclusion of this treatment, he had significant improvement in his right sided weakness. He was able to ambulate without any assistance and did not require the use of a cane. He regained sufficient strength in his arm to allow him to feed himself and address issues of personal hygiene without any assistance. In the almost five years since his treatment he has maintained these gains.

Patient B

At 55 years old, Patient B suffered a left hemispheric subcortical stroke in March 1998 leaving him with slurred speech and right sided weakness. He underwent conventional post stroke treatment and rehabilitation. At the time of his discharge from conventional treatment, Patient B had moderate right leg weakness which produced a difficult and abnormal gait. This limited his mobility and required use of assistive devices such as cane, walker or wheelchair for all but the shortest of distances. He had no real use of his arm and required assistance with personal hygiene and anything necessitating the use of his right arm or hand.

In September of 1999, approximately 18 months after his stroke, Patient B began treatment under the above described methodology. Specifically, the treatment method included the steps of:

determining the muscles to be treated;

coating the skin with electro-conductive gel;

passing a probe connected to the RSD over the muscle using sufficient current to elicit a muscle contraction thereby indicating the location of a motor point;

marking the motor point;

removing the gel with alcohol swabs;

inserting conductive needles into the proximal 40 and distal 50 motor points;

connecting the needles to the RSD;

applying current having a carrier frequency of 2500 Hz to the needles to stimulate the muscle.

He was treated 15 minutes per day, five days a week for approximately twelve months. The muscles treated included the quadriceps, hamstrings, biceps, triceps, wrist extensors and wrist flexors. He was treated utilizing needles for the first four months and then converted to surface pad stimulation. During the stimulation step, he initially tolerated less than 1 mA and gradually increased the current up to approximately 10 mA. At the conclusion of his treatment, he had only minimal weakness in his right arm and leg. He was able to walk prolonged distances without assistance and at normal speeds. He regained sufficient use of his arm to allow the performance of normal daily activities, including issues of personal hygiene, without any assistance. In the two and a half years since he completed his treatment, he has maintained his functional gains.

Patient C

Patient C, a 70 year old white male, suffered a right hemispheric stroke in May 1996. He received conventional post stroke care and rehabilitation. At the time of his discharge from this conventional care he was left with significant left sided weakness. This resulted in severe limitations of both ambulation and performing activities of daily living. Patient C required the use of a wheelchair and had virtually no use of his left arm. This made even simple issues of personal hygiene impossible.

In September of 1997, approximately 16 months after his stroke, Patient C began treatment under the above described methodology. Specifically, the treatment method included the steps of:

determining the muscles to be treated;

coating the skin with electro-conductive gel;

passing a probe connected to the RSD over the muscle using sufficient current to elicit a muscle contraction thereby indicating the location of a motor point;

marking the motor point;

removing the gel with alcohol swabs;

inserting conductive needles into the proximal 40 and distal 50 motor points;

connecting the needles to the RSD;

applying current having a carrier frequency of 2500 Hz to the needles to stimulate the muscle.

He was treated 15 minutes per day, five days a week for approximately twelve months. Treated muscles included quadriceps, hamstrings, tibialis anterior, peroneus longus, biceps, triceps, wrist extensors and wrist flexors. During the stimulation step, he initially tolerated 1 mA and eventually worked up to approximately 15 mA. His stimulation used needles throughout almost the entire twelve months of treatment. At the conclusion of his treatment he made remarkable progress and was able to walk independently without the use of any assistive devices. He regained sufficient use of his arm to allow the performance of almost all daily functions and issues of personal hygiene. He has maintained these improvements and now plays golf twice a week.

Patient D

Patient D suffered a left hemispheric cortical stroke in the spring of 2000 at the age of 65. He had a past medical history significant for cardiovascular heart disease, smoking and alcohol consumption which lead to significant carotid artery blockage. His carotid artery blockage ultimately led to his stroke. He received conventional post stroke care and rehabilitation including surgery to correct the carotid artery blockage.

At the time of discharge from his rehabilitation Patient D had significant right sided weakness with spasticity (increased muscle tone) and aphasia (loss of language function). He was ambulatory without assistive devices but did have moderate gait deviations. He had limitations in both foot elevation and isolated hip flexion which created functional loss. His primary complaint regarding his leg function was poor leg strength and stamina during ambulation. However, his prime concern overall was his right arm weakness and spasticity. He presented with spasticity throughout his entire right arm. Arm elevation was limited severely by his hypertonic state, joint (shoulder, elbow and wrist) restrictions, and accommodated muscle shortening. This lead to an usual arm position in which his upper arm was held close to his side with his elbow flexed at greater than 90 degrees. These severe limitations presented problems with passive movements as well. He also suffered from a severe aphasia that was primarily expressive (inability to produce speech) with some receptive (inability to interpret language) component as well. His vocabulary at that time was approximately eight words while his interpretive ability was about 80% of normal. Most of this receptive disability was related to understanding time and numbers.

In July 2002, approximately 26 months after his stroke, Patient D began treatment under the above described methodology. He continues in therapy to this day. His therapy has been 5 days per week with periods of rest every 4-6 weeks. The treatment method included the steps of:

determining the muscles to be treated;
coating the skin with electro-conductive gel;
passing a probe connected to the RSD over the muscle using sufficient current to elicit a muscle contraction thereby indicating the location of a motor point;
marking the motor point;
removing the gel with alcohol swabs;
inserting conductive needles into the proximal 40 and distal 50 motor points;
connecting the needles to the RSD;
applying current having a carrier frequency of 2500 Hz to the needles to stimulate the muscle.

The treated muscles include biceps, triceps, wrist extensors, wrist flexors, quadriceps and hamstrings. His stimulation was accomplished over periods of 15 minutes per day, using needles for the first six months and then changed to surface pads. Since the first six months only his arm has been treated because his leg function was sufficiently improved at that point no further therapy was required. He has only tolerated up to approximately 5 mA, but has shown good muscle contractions and progress. Speech therapy has been an integral part of his work here and he has demonstrated outstanding improvements. Patient D can formulate and speak intermittently with a relatively unlimited vocabulary. He is now producing spontaneous speech which is occurring on a regular basis. His speech therapist contributes much of his improvements in this area to the physical therapy and associated muscle stimulation.

Functionally, his lower extremity function has improved as his strength and walking stamina has doubled. He no longer suffers with "toe stubbing" because of his foot elevation weakness. The majority of his treatment has surrounded relieving upper extremity spasticity, increasing passive joint mobility and elongating shortened muscles. He has experienced significant improvement in all of these areas. Currently he can elevate his arm at or above his forehead. Abduction (arm elevation out to the side) has increased two times. Passive shoulder movement is greater than 70% of normal. Severely limited passive elbow motion has been relieved. He can achieve 70-80% of normal passive elbow movement. Active movement continues to be significantly limited because of his spasticity. Recently Botox injections were administered to his right arm to try and help relieve this spasticity. He is responding well to this treatment and we are now utilizing a dynamic splint to facilitate lengthening of his biceps and other arm flexors. This will allow him to begin swinging a golf club in the very near future. He demonstrates an eagerness to continue his work and progress. He is confident that he will "hit that golf ball" before he is finished.

Patient E

Patient E suffered a brainstem stroke on Apr. 17, 2001. He was noted at that time to have significant right carotid artery blockage and underwent surgery to correct that blockage. He received conventional post stroke treatment and rehabilitation immediately following his stroke.

At the time of his discharge from conventional stroke rehabilitation Patient E showed both upper and lower extremity deficits. He ambulated with the use of a quad cane performing at a moderate to poor level. Deviations in his gait centered on his inability to perform active hip flexion (lifting the upper leg up from a seated position), knee flexion (actively bending the knee) and ankle dorsiflexion (ability to lift his foot). These deficits manifest into a gait in which the patient will be unbalanced and will "stub" his toe on the recovery or "swing through" portion of the gait cycle. This was particularly troubling for Patient E given his very specific work environment. He is a rancher who makes his living riding a horse and walking on uneven terrain. He is also an accomplished cutting horse rider and has been training cutting horses for competition and sale since the 1960's.

The upper extremity deficits which demonstrated by Patient E included an inability to elevate his shoulder to 90 degrees (parallel to the floor). He showed significant weakness when performing resisted elbow flexion and extension as well as a general inability to supinate and pronate his forearm (rotate palm up to palm down). He demonstrated little to no active wrist movement and severe spasticity in his hand. Increased spasticity in his hand has left a functionally poor position and poor grip ability with his fingers. It should be noted that he also presented with significant limitations because of orthopedic joint restrictions and muscle/tendon complex shortening. He was able to sit on his horse independently but required maximum assistance from 2-3 people to mount and dismount. During the initial days of his therapy he was unable to drive to his sessions and required daily assistance from his wife to get dressed as well as performing simple tasks of personal hygiene.

In October of 2002, approximately 18 months after his stroke, Patient E began treatment under the above described methodology. Specifically, the treatment method included the steps of:
determining the muscles to be treated;
coating the skin with electro-conductive gel;
passing a probe connected to the RSD over the muscle using sufficient current to elicit a muscle contraction thereby indicating the location of a motor point;
marking the motor point;
removing the gel with alcohol swabs;
inserting conductive needles into the proximal 40 and distal 50 motor points;
connecting the needles to the RSD;
applying current having a carrier frequency of 2500 Hz to the needles to stimulate the muscle.

The muscles treated have included biceps, triceps, deltoid, quadriceps, hamstrings, wrist flexors, wrist extensors and tibialis anterior. The treatment has been accomplished over periods of 15 minutes per day using needles up to the current time. The tibialis anterior was treated for six weeks until the patient could walk independently. This muscle has not been treated since that time. He tolerated up to approximately 18 mA of current. Over the past 6 months, he has only been seen for 35 visits. The limited number of treatments has not precluded his progress. At this time, he ambulates with no assisted devices and with significantly improved gait. He has a current ability to actively hip flex and can now lie prone (on his stomach) and flex his knee to near 90 degrees. This is significant as these movements are primary for riding a horse, in particular a cutting horse. His ability to ambulate is also improved as he can do so without "stubbing his toe." This improvement is due to both increases in his ability to flex his hip and to lift his foot during the recovery portion of the gait cycle. Upper extremity improvements are seen in all areas of the upper limb. He has improved his ability to elevate his shoulder at and above 90 degrees (parallel to the floor). Biceps strength is improved as the patient demonstrates greater ability to flex his elbow. Active wrist movement has increased two times and his grip strength is such that he is holding, with moderate ability, the reign and saddle horn while riding. He indicates that he can now mount and dismount his horse independently, although with great difficulty. Once mounted, he can ride at a level indistinguishable to friends and family from his pre-stroke days. This is a very significant improvement. His ability to mount and ride independently provides a significant level of patient independence and a return to some activities of daily living. This improved limb function has also provided for improved trunk control. This new found trunk stability will hopefully allow for his return to cutting horse competition and training.

Clearly, the above case studies demonstrate the ability of the current invention to significantly improve the quality of life of stroke victims. Other embodiments of the current invention will be apparent to those skilled in the art from a consideration of this specification or practice of the invention disclosed herein. However, the foregoing specification is considered merely exemplary of the current invention with the true scope and spirit of the invention being indicated by the following claims.

We claim:

1. A method for restoring functionality to muscles weakened and atrophied by cerebrovascular disease comprising the steps of:
    selecting the muscle to be treated and determining the proximal and distal motor points of said muscle;
    providing at least two electrically conductive needles, each needle having a length of about 25 to about 75 mm;
    inserting at least one electrically conductive needle a depth sufficient to extend into the area of the proximal motor point of said muscle;
    inserting at least one electrically conductive needle a depth sufficient to extend into the area of the distal motor point of said muscle;
    connecting the needles to a source of electricity, said source of electricity suitable for providing a two second electric current ramp up and a two second electric current ramp down; and,
    electrically stimulating said muscle by applying an electric current through the needles to said muscle said electric current having a carrier frequency of about 2500 Hz, wherein said step of electrically stimulating said muscle includes a two second electric current ramp up and a two second electric current ramp down.

2. The method of claim 1, wherein said electric current is applied at a rate between about 40 pulses per second and about 60 pulses per second.

3. The method of claim 2, wherein each pulse has a pulse width between about 200 microseconds and about 350 microseconds.

4. The method of claim 1, further comprising the step of cycling the application of said electric current between periods of stimulation and rest.

5. The method of claim 4, wherein said electric current is cycled between periods of stimulation and rest for a period of about 5 minutes to about 15 minutes.

6. The method of claim 5, wherein during said step of cycling the application of electric current, the stimulation step is from about 5 seconds to about 50 seconds and the rest step is about 5 seconds to about 50 seconds.

7. The method of claim 4, wherein said periods of stimulation and rest continue for up to about 15 minutes.

8. The method of claim 7, wherein during said step of cycling the application of electric current, the stimulation step is from about 10 seconds and the rest step is about 10 seconds.

9. The method of claim 1, wherein the electric current is sufficient to produce a visible muscle contraction.

10. The method of claim 1, further comprising the step of identifying specific muscles requiring rehabilitation.

11. The method of claim 1, wherein said needle inserted in said proximal motor point is connected by means of a first lead to the source of electricity and said needle inserted in said distal motor point is connect by means of a second lead to the source of electricity.

12. The method of claim 1, further comprising the application of electro-conductive gel to the skin over said muscle prior to locating the proximal and distal motor points.

13. The method of claim 12, further comprising the step of moving an electric probe over the electro-conductive gel in the general region of the distal motor point until a contraction within the muscle is noted and marking said distal motor point.

14. The method of claim 12, further comprising the step of moving an electric probe over the electro-conductive gel in the general region of the proximal motor point until a contraction within the muscle is noted and marking said proximal motor point.

15. The method of claim 12, further comprising the step of removing said electro-conductive gel prior to inserting said needles into said motor points.

16. The method of claim 1, wherein said steps of inserting electrically conductive needles into the proximal and distal motor points, connecting the needles to a source of electricity, and, electrically stimulating the muscle by applying an electric current with a frequency of about 2500 Hz is repeated about 3 times per week.

17. The method of claim 16, wherein said method is carried out for at least three months.

18. The method of claim 1, further comprising the step of administering physical therapy directed to the rehabilitation of the treated muscle.

19. The method of claim 1, wherein the current is applied at about 50 pulses per second.

20. The method of claim 1, wherein each pulse has a pulse width of 300 microseconds.

21. A method for restoring functionality to muscles weakened and atrophied by cerebrovascular disease comprising the steps of:
    selecting the muscle to be treated;
    providing at least two electrically conductive needles, each needle having a length of about 25 to about 75 mm;
    inserting at least one electrically conductive needle a depth sufficient to extend into the area of the proximal motor point of said muscle;
    inserting at least one electrically conductive needle a depth sufficient to extend into the area of the distal motor point of said muscle;
    connecting the needles to a source of electricity, said source of electricity suitable for providing a two second electric current ramp up and a two second electric current ramp down and said source of electricity provides an electric current having a biphasic waveform which is delivered at about 40 pulses to 60 pulses per second with a pulse width of 200 to 350 microseconds;
    electrically stimulating said muscle by applying an electric current through the needles to said muscle, the electric current having a carrier frequency of about 2500 Hz, wherein said step of electrically stimulating said muscle includes a two second electric current ramp up and a two second electric current ramp down, the current being applied as a biphasic waveform at a pulses per second count between about 40 and about 60 pulses per second with each pulse having between about 200 to about 350 microsecond pulse width; and, cycling the application of current between periods of stimulation and rest for about 5 minutes to about 15 minutes, wherein the stimulation period is about 5 seconds to about 50 seconds and the rest period is about 5 seconds to about 50 seconds.

22. The method of claim 21, wherein the electric current is sufficient to produce a visible muscle contraction.

23. The method of claim 21, further comprising the steps of determining the proximal and distal motor points of said muscle.

24. The method of claim 23, further comprising the application of electro-conductive gel to the skin over said muscle prior to locating the proximal and distal motor points.

25. The method of claim 24, further comprising the step of moving an electric probe over the electro-conductive gel in the general region of the distal motor point until a contraction within the muscle is noted and marking said distal motor point.

26. The method of claim 24, further comprising the step of moving an electric probe over the electro-conductive gel in the general region of the proximal motor point until a contraction within the muscle is noted and marking said proximal motor point.

27. The method of claim 24, further comprising the step of removing said electro-conductive gel prior to inserting said needles into said motor points.

28. The method of claim 21, wherein said steps of inserting electrically conductive needles into the proximal and distal motor points, connecting the needles to a source of electricity, and, electrically stimulating the muscle by applying an electric current with a frequency of about 2500 Hz is repeated about 5 times per week.

29. The method of claim 28, wherein said method is carried out for at least three months.

30. The method of claim 21, further comprising the step of administering physical therapy directed to the rehabilitation of the treated muscle.

31. The method of claim 21, wherein the cerebrovascular disease is any ischemic, anoxic, traumatic or infectious injury to the brain.

32. The method of claim 21, wherein the current is applied at about 50 pulses per second.

33. The method of claim 21, wherein each pulse has a pulse width of 300 microseconds.

34. The method of claim 21, wherein said periods of stimulation and rest continue for up to about 15 minutes.

35. The method of claim 34, wherein during said step of cycling the application of electric current, the stimulation step is from about 10 seconds and the rest step is about 10 seconds.

36. A method for restoring functionality to muscles weakened and atrophied by cerebrovascular disease comprising the steps of:
  selecting the muscle to be treated;
  providing at least two electrically conductive needles, each needle having a length of about 25 to about 75 mm;
  inserting at least one electrically conductive needle a depth sufficient to extend into the area of the proximal motor point of said muscle;
  inserting at least one electrically conductive needle a depth sufficient to extend into the area of the distal motor point of said muscle;
  connecting the needles to a source of electricity, said source of electricity suitable for providing a two second electric current ramp up and a two second electric current ramp down and said source of electricity provides an electric current having a biphasic waveform which is delivered at about 40 pulses to 60 pulses per second with a pulse width of 200 to 350 microseconds;
  electrically stimulating said muscle by applying an electric current through the needles to said muscle, the electric current having a carrier frequency of about 2500 Hz, wherein said step of electrically stimulating said muscle includes a two second electric current ramp up and a two second electric current ramp down, the current being applied as a biphasic waveform at a pulses per second count between about 40 and about 60 pulses per second with each pulse having between about 200 to about 350 microsecond pulse width; and,
  cycling the application of current between periods of stimulation and rest for about 5 minutes to about 15 minutes, wherein the stimulation period is about 5 seconds to about 50 seconds and the rest period is about 5 seconds to about 50 seconds, and, wherein said stimulation period includes a 2 second current ramp up and a 2 second current ramp down.

37. The method of claim 36, wherein the electric current is sufficient to produce a visible muscle contraction.

38. The method of claim 36, further comprising the steps of determining the proximal and distal motor points of said muscle.

39. The method of claim 38, further comprising the application of electro-conductive gel to the skin over said muscle prior to locating the proximal and distal motor points.

40. The method of claim 39, further comprising the step of moving an electric probe over the electro-conductive gel in the general region of the distal motor point until a contraction within the muscle is noted and marking said distal motor point.

41. The method of claim 39, further comprising the step of moving an electric probe over the electro-conductive gel in the general region of the proximal motor point until a contraction within the muscle is noted and marking said proximal motor point.

42. The method of claim 39, further comprising the step of removing said electro-conductive gel prior to inserting said needles into said motor points.

43. The method of claim 36, wherein said steps of inserting electrically conductive needles into the proximal and distal motor points, connecting the needles to a source of electricity, and, electrically stimulating the muscle by applying an electric current with a frequency of about 2500 Hz is repeated about 5 times per week.

44. The method of claim 43, wherein said method is carried out for at least three months.

45. The method of claim 36, further comprising the step of administering physical therapy directed to the rehabilitation of the treated muscle.

46. The method of claim 36, wherein the cerebrovascular disease is any ischemic, anoxic, traumatic or infectious injury to the brain.

47. The method of claim 36, wherein the current is applied at about 50 pulses per second.

48. The method of claim 36, wherein each pulse has a pulse width of 300 microseconds.

49. The method of claim 36, wherein during said step of cycling the application of electric current, the stimulation step is from about 10 seconds and the rest step is about 10 seconds.

50. A method for restoring functionality to muscles weakened and atrophied by cerebrovascular disease comprising the steps of:
- selecting the muscle to be treated;
- providing at least two electrically conductive needles, each needle having a length of about 25 to about 75 mm;
- inserting at least one electrically conductive needle a depth sufficient to extend into the area of the proximal motor point of said muscle;
- inserting at least one electrically conductive needle a depth sufficient to extend into the area of the distal motor points of said muscle;
- connecting said needles to a source of electricity, said source of electricity suitable for providing a two second electric current ramp up and a two second electric current ramp down and said source of electricity provides an electric current having a biphasic waveform which is delivered at about 50 pulses per second with a pulse width of 300 microseconds;
- electrically stimulating said muscle by applying an electric current through said needles to said muscle, the electric current having a frequency of about 2500 Hz, the current being applied as a biphasic waveform at about 50 pulses per second with about a 300 microsecond pulse width;
- cycling the application of current between periods of stimulation and rest for about 15 minutes, wherein the stimulation period is about 10 seconds and the rest period is about 10 seconds wherein said stimulation period includes a 2 second current ramp up and a 2 second current ramp down.

51. The method of claim 50, wherein the electric current is sufficient to produce a visible muscle contraction.

52. The method of claim 50, further comprising the steps of determining the proximal and distal motor points of said muscle.

53. The method of claim 52, further comprising the application of electro-conductive gel to the skin over said muscle prior to locating the proximal and distal motor points.

54. The method of claim 53, further comprising the step of moving an electric probe over the electro-conductive gel in the general region of the distal motor point until a contraction within the muscle is noted and marking said distal motor point.

55. The method of claim 53, further comprising the step of moving an electric probe over the electro-conductive gel in the general region of the proximal motor point until a contraction within the muscle is noted and marking said proximal motor point.

56. The method of claim 53, further comprising the step of removing said electro-conductive gel prior to inserting said needles into said motor points.

57. The method of claim 50, wherein said method is carried out for at least twelve months.

58. The method of claim 50, further comprising the step of administering physical therapy directed to the rehabilitation of the treated muscle.

59. The method of claim 50, wherein the cerebrovascular disease is any ischemic, anoxic, traumatic or infectious injury to the brain.

60. The method of claim 1, wherein said source of electricity is a Russian Stimulation Device.

61. The method of claim 21, wherein said source of electricity is a Russian Stimulation Device.

62. The method of claim 36, wherein said source of electricity is a Russian Stimulation Device.

63. The method of claim 50, wherein said source of electricity is a Russian Stimulation Device.

* * * * *